(12) United States Patent
Holderby et al.

(10) Patent No.: US 11,357,621 B2
(45) Date of Patent: Jun. 14, 2022

(54) LEVER-ACTUATED DRIVE

(71) Applicant: Alcon Inc., Fribourg (CH)

(72) Inventors: Victoria Holderby, Arlington, TX (US); Douglas Brent Wensrich, Bedford, TX (US)

(73) Assignee: Alcon Inc., Fribourg (CH)

( * ) Notice: Subject to any disclaimer, the term of this patent is extended or adjusted under 35 U.S.C. 154(b) by 43 days.

(21) Appl. No.: 16/941,381

(22) Filed: Jul. 28, 2020

(65) Prior Publication Data

US 2021/0038372 A1 Feb. 11, 2021

Related U.S. Application Data

(60) Provisional application No. 62/883,441, filed on Aug. 6, 2019.

(51) Int. Cl.
*A61F 2/16* (2006.01)

(52) U.S. Cl.
CPC .... *A61F 2/1662* (2013.01); *A61F 2002/1683* (2013.01)

(58) Field of Classification Search
CPC .... A61F 2/1662; A61F 2/1664; A61F 2/1667; A61F 2/167; A61F 2/1672; A61F 2/1675; A61F 2/1678; A61F 2002/1681; A61F 2002/1683; A61F 2002/169; A61B 17/3468; A61B 17/2909; A61B 2017/2918; A61M 37/0069
See application file for complete search history.

(56) References Cited

U.S. PATENT DOCUMENTS

| | | | |
|---|---|---|---|
| 9,364,316 B1 | 6/2016 | Kahook et al. | |
| 2005/0101967 A1* | 5/2005 | Weber | A61M 37/0069 606/107 |
| 2017/0319332 A1 | 11/2017 | Kahook et al. | |

* cited by examiner

*Primary Examiner* — Majid Jamialahmadi

(57) ABSTRACT

Systems, methods, and devices for inserting an intraocular lens (IOL) assembly into an eye may be provided. An apparatus for delivery of a lens component into an eye, including: a nozzle; a housing, wherein the nozzle is operatively coupled to the housing; a first lever; a second lever; and a linkage assembly. The linkage assembly may be disposed within the housing between and adjacent to the first and second levers. The linkage assembly may include a plurality of linkages pivotably coupled to each other, wherein the linkage assembly is collapsible.

11 Claims, 10 Drawing Sheets

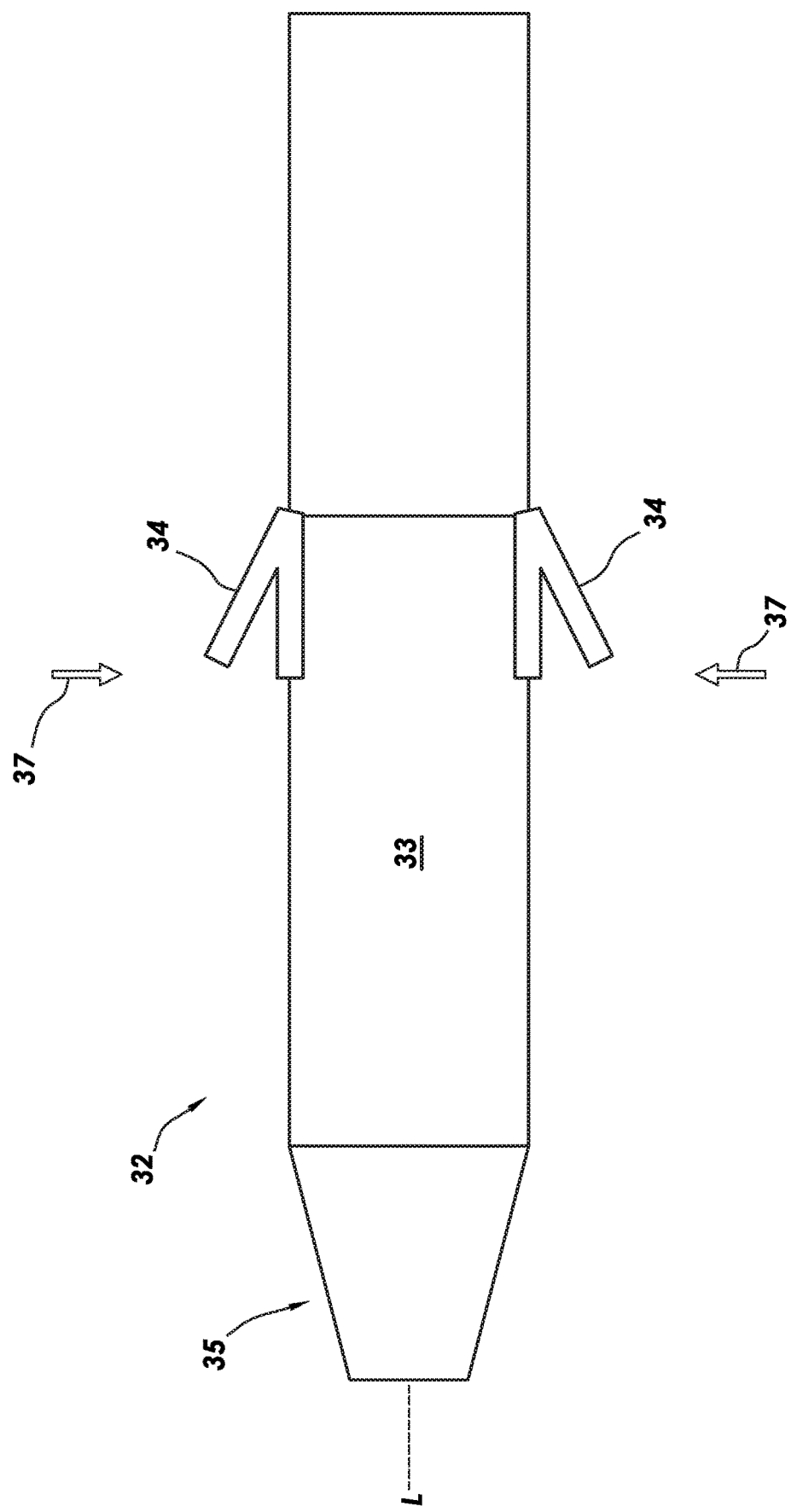

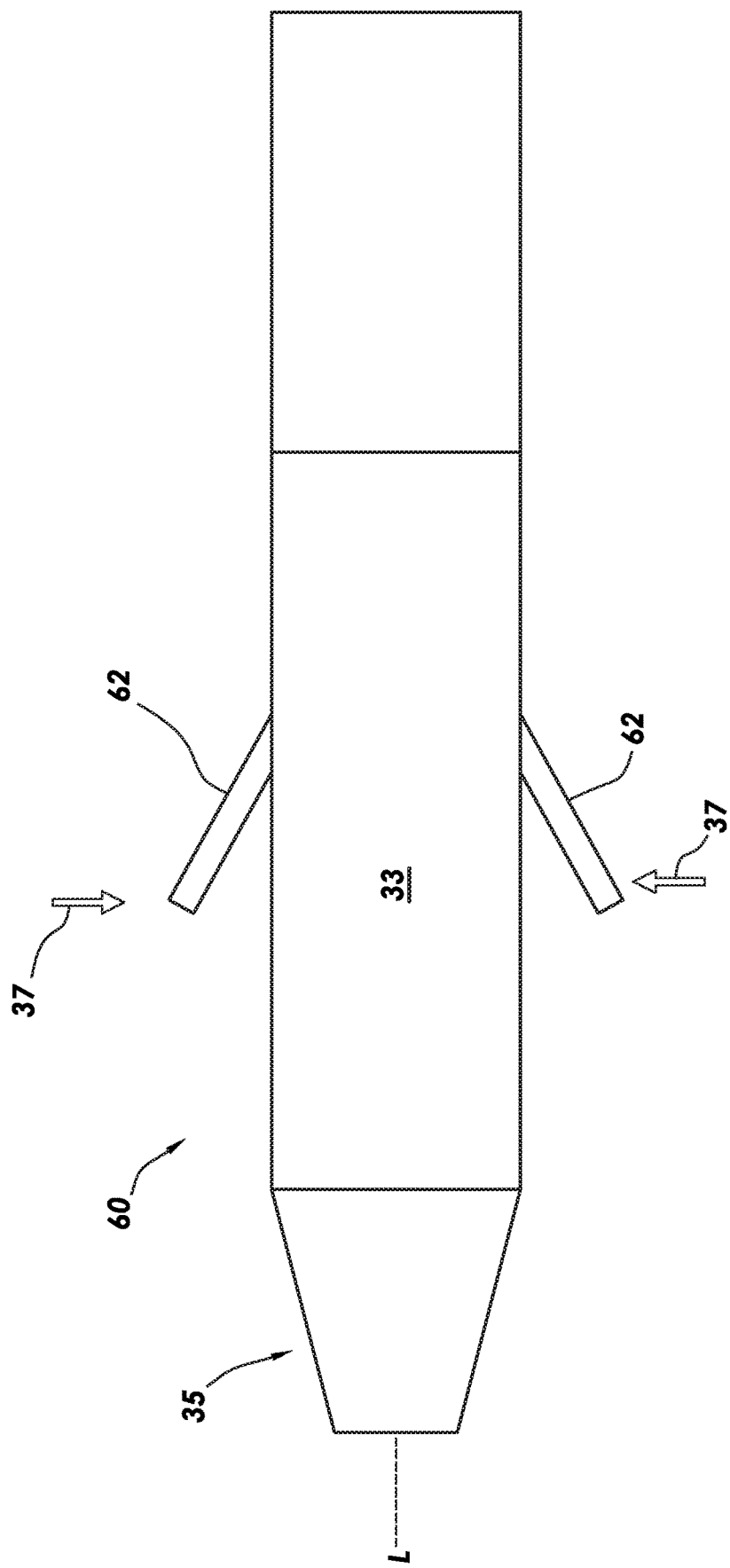

LEVER-ACTUATED DRIVE

TECHNICAL FIELD

The present disclosure generally relates to eye surgery and, more particularly, embodiments may generally relate to systems, methods, and devices for inserting an intraocular lens (IOL) into an eye that employ a lever-actuated drive.

BACKGROUND

The human eye can suffer a number of maladies causing mild deterioration to complete loss of vision. While contact lenses and eyeglasses can compensate for some ailments, ophthalmic surgery may be required for others. Generally, ophthalmic surgery may be classified into posterior segment procedures, such as vitreoretinal surgery, and anterior segment procedures, such as cataract surgery. Vitreoretinal surgery may address many different eye conditions, including, but not limited to, macular degeneration, diabetic retinopathy, diabetic vitreous hemorrhage, macular hole, detached retina, epiretinal membrane, and cytomegalovirus retinitis.

For cataract surgery, a surgical procedure may require incisions and insertion of tools within an eye to replace the clouded lens with an intraocular lens (IOL). An insertion tool can be used for delivery of the IOL into the eye. By way of example, the insertion tool may include a plunger for forcing the IOL out of the nozzle of the insertion tool. In some instances, the IOL may be pre-loaded in the insertion tool. In other instances, a separate bay may be loaded into the insertion tool. The plunger may engage the IOL to advance the IOL from the bay, through the nozzle, and into the eye. The bay (or insertion tool) may include a folding chamber configured to cause the IOL to fold, for example, when the IOL advances through the folding chamber. In some instances, a separate action may cause folding of the IOL.

Delivery of the IOL from the insertion tool can be a multi-step process. For example, the delivery may include two stages, which may be referred to as an advancing stage and a delivery stage. In the advancing stage, the IOL can be advanced from a storage position in the bay to a dwell position. The IOL may be pre-folded or may be folded when advanced from the storage position to the dwell position. At the dwell position, advancement of the IOL may be halted, the nozzle positioned in the eye, the IOL may then be further advanced from the dwell position, in the delivery stage, which may include advancing the IOL through the nozzle and into the eye.

SUMMARY

In an exemplary embodiment, the present disclosure provides an apparatus for delivery of a lens component into an eye, including: a nozzle; a housing, wherein the nozzle is operatively coupled to the housing; a first lever; a second lever; and a linkage assembly. The linkage assembly may be disposed within the housing between and adjacent to the first and second levers. The linkage assembly may include a plurality of linkages pivotably coupled to each other, wherein the linkage assembly is collapsible.

In another exemplary embodiment, the present disclosure provides an apparatus for delivery of a lens component into an eye, including a nozzle; a housing, wherein the nozzle is operatively coupled to the housing; a first lever movably coupled to the housing; a second lever movably coupled to the housing; a linkage assembly disposed within the housing between the first and second levers; a passage positioned at a first end of the linkage assembly; and a rod coupled to a second end of the linkage assembly, the rod axially aligned with the passage. The linkage assembly may include linkages pivotably coupled to each other, wherein the first and second levers are pivotably coupled to the linkage assembly.

In another exemplary embodiment, the present disclosure provides a method for delivery of a lens component into an eye, including inserting a nozzle of an insertion tool into the eye, wherein the inversion tool includes a housing, wherein the nozzle is operatively coupled to the housing; a first lever; a second lever; a linkage assembly disposed within the housing between and adjacent to the first and second levers, and a shaft extending from the linkage assembly in a direction toward the nozzle. The linkage assembly may include a plurality of linkages pivotably coupled to each other. The method may further include depressing the first and second levers. The method may further include moving the shaft through the nozzle.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTION OF THE DRAWINGS

These drawings illustrate certain aspects of some of the embodiments of the present disclosure and should not be used to limit or define the disclosure.

FIG. 4A is a side view of an insertion tool including a scissor-type mechanism, in accordance with embodiments of the present disclosure;

FIG. 5A illustrates an insertion tool including a reverse jack-type mechanism, in accordance with embodiments of the present disclosure;

DETAILED DESCRIPTION

Figure 1:
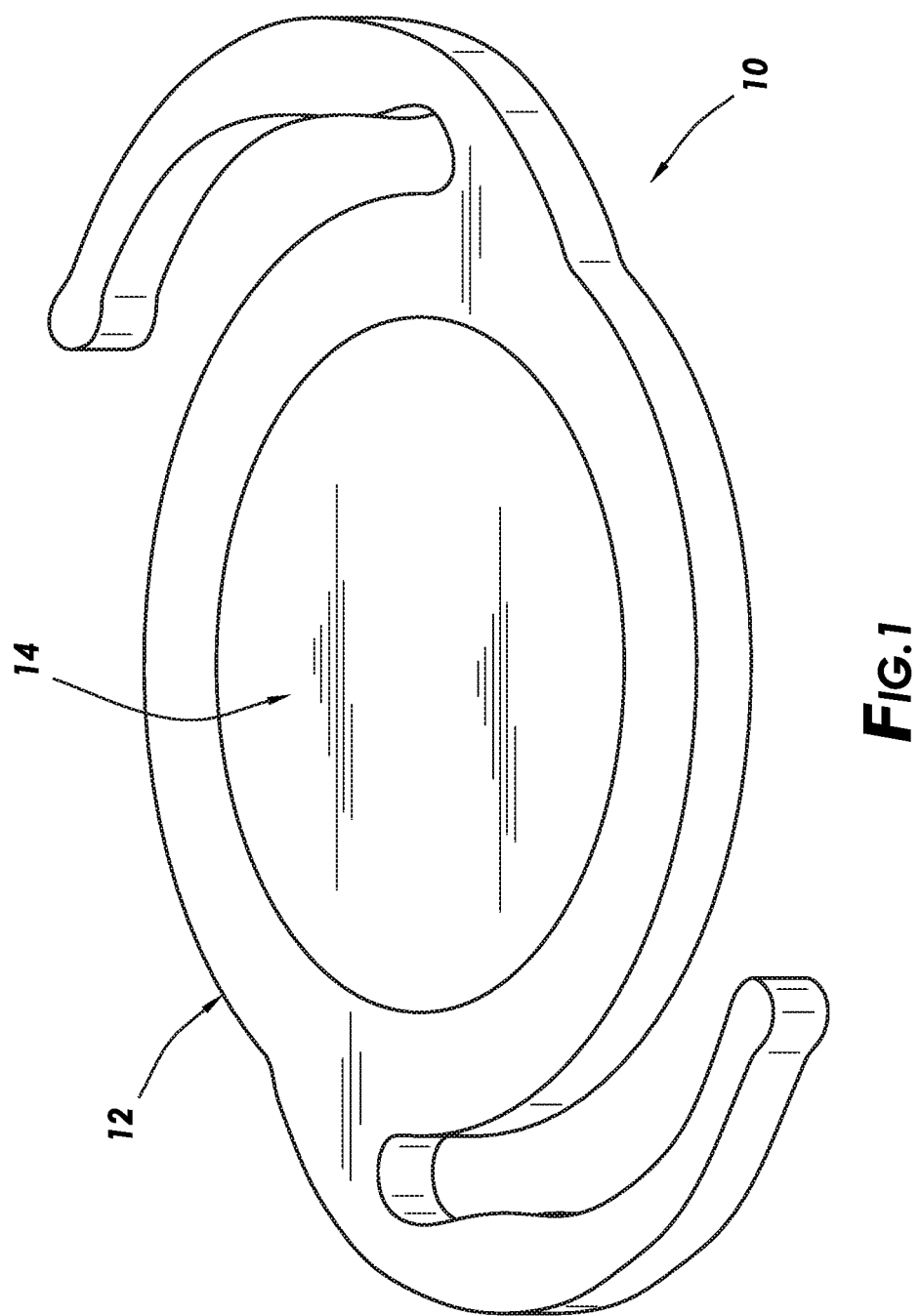
FIG. 1 illustrates a modular IOL with a lens portion positioned in a base portion in accordance with embodiments of the present disclosure.

For the purposes of promoting an understanding of the principles of the present disclosure, reference will now be made to the implementations illustrated in the drawings and specific language will be used to describe them. It will nevertheless be understood that no limitation of the scope of the disclosure may be intended. Any alterations and further modifications to the described devices, instruments, methods, and any further application of the principles of the present disclosure are fully contemplated as would normally occur to one skilled in the art to which the disclosure relates. In particular, it may be fully contemplated that the features, components, and/or steps described with reference to one or more implementations may be combined with the features, components, and/or steps described with reference to other implementations of the present disclosure. For simplicity, in some instances the same reference numbers are used throughout the drawings to refer to the same or like parts.

Embodiments of the present disclosure may include advancing the IOL from an insertion tool via a linkage assembly including pivotable linkages. (e.g., a scissor mechanism and/or a reverse car jack mechanism) actuated by levers. In certain embodiments, as the levers are depressed, the levers pivot the linkages causing the linkage assembly to extend longitudinally. This advances the IOL out of the nozzle of the insertion tool. Particular embodiments may include a threaded rod that advances the IOL as the levers are depressed.

Any suitable IOL may be used, including, but not limited to, IOLs that include a lens portion and haptic extensions. The haptic extensions may be side struts (or other suitable extensions) that extend from the lens portion to hold the lens portion in place when implanted in the eye. In at least one embodiment, the IOL may be modular. Embodiments of a modular IOL may include a base portion and a lens portion. The base portion may include the haptic extensions. The lens portion may be coupled to the base portion to form the modular IOL.

FIG. 1 illustrates an embodiment of a modular IOL 10. The modular IOL 10 may be any suitable modular interocular lens. As illustrated, the modular IOL 10 may include a base portion 12 and a lens portion 14. In the illustrated embodiment, the lens portion 14 is positioned in the base portion 12. In operation, the modular IOL 10 can allow for the lens portion 14 to be modified or adjusted while leaving the base portion 12 in place, either intra-operatively or post-operatively. By way of example, the modular IOL 10 may be implanted into an eye. After implantation, the lens portion 14 may be modified, adjusted, and/or replaced while leaving the base portion 12 positioned in the eye. In at least one embodiment, the modular IOL 10 may be assembled in the eye. For example, the base portion 12 may first be implanted in the eye. The lens portion 14 may then be delivered into the eye and attached to the base portion 12.

Figure 2:
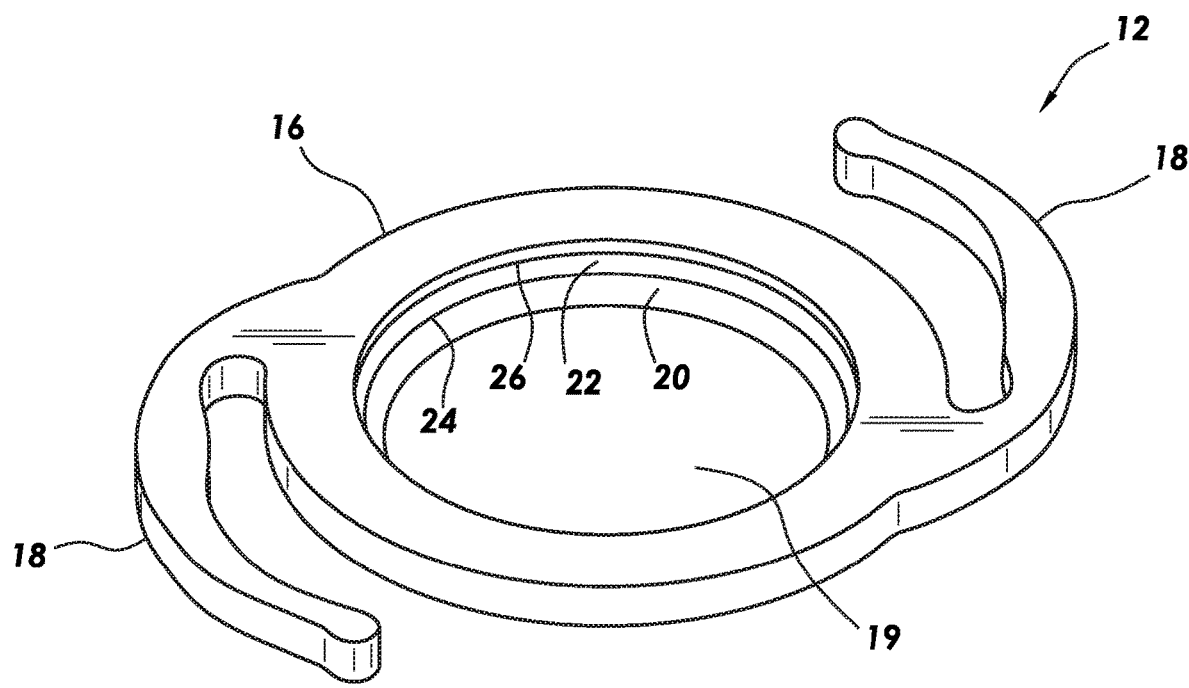
FIG. 2 illustrates a base portion of a modular IOL in accordance with embodiments of the present disclosure.

FIG. 2 illustrates the base portion 12 of the modular IOL 10 of FIG. 1 in accordance with embodiments of the present disclosure. In the illustrated embodiment, the base portion 12 includes a base 16 and haptic extensions 18. The haptic extensions 18 may be side struts (or other suitable extensions) extending from the base 16 that may stabilize the base portion 12 when it may be disposed within the patient's eye. In the illustrated embodiment, the base 16 may define a hole 19, which may be centrally located in the base 16 as shown on FIG. 2. While the hole 19 is shown as a through hole extending through the base 16, embodiments also contemplate hole 19 being a blind hole that does not extend through the base 16. For example, the base 16 may be a solid disc with the hole 19 being a blind hold that does not extend through the base 16, rather than an annular ring with the hole 19 extending through the base 16. Hole 19 may be defined by inner perimeter surface 20 of the base 16. In at least one embodiment, a recessed groove 22 is formed in inner perimeter surface 20. Recessed groove 22 may include a lower rim 24 and an upper rim 26. The upper rim 26 may have an insider diameter that is the same as or greater than the outside diameter of the lens portion 14 (excluding tabs 30 shown on FIG. 3) such that the lens portion 14 can rest inside the hole 19 of the base 16. All or a portion of the lower rim 24 can have an inside diameter that is less than the outside diameter of the lens portion 14 (excluding tabs 30 shown on FIG. 3) such that the lower rim 24 can act as a ledge or backstop for the lens portion 14 when placed in the hole 19 of the base 16. The base portion 12 may be unitary or may be formed from component parts that are combined or attached in any suitable manner.

Figure 3:
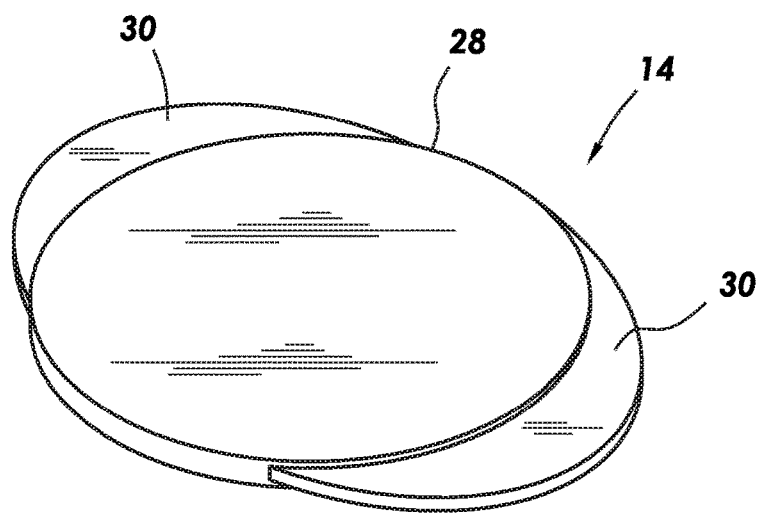
FIG. 3 illustrates a lens portion of a modular IOL in accordance with embodiments of the present disclosure.

With reference to FIG. 3, the lens portion 14 of the modular IOL 10 of FIG. 1 is illustrated in accordance with embodiments of the present disclosure. In the illustrated embodiments, the lens portion 14 includes an optic portion 28 and one or more tabs 30. While FIG. 3 illustrates two of the tables, embodiments may include only one of the tabs 30 or alternatively three, four, or more of the tabs 30. In addition, the tabs 30 on the lens portion 14 may be the same or different from one another. The tabs 30 are shown as being fixed to the optic portion 28; however, it should be understood that one or more of the tabs 30 may be actuated to move from a compressed position for delivery into the hole 19 of the base 16 (e.g., shown on FIG. 2) to an uncompressed extended position for deployment into the recessed groove 22 of the base 16 (e.g., shown on FIG. 2), thus forming an interlocking connection between the base portion 12 and the lens portion 14. The outside curvature of the tabs 30 may have a radius conforming to the inside radius of the recessed groove 22. This arrangement should limit relative movement between the base portion 12 and the lens portion 14 once connected. In embodiments, a suitable optic portion 28 may be in a shape similar to that of a natural lens within the eye and made from a suitable material such as silicone, acrylic, and/or combinations thereof. While the optic portion 28 is shown as being circular, the optic portion 28 may be any suitable shape, such as oval or ellipsoidal, for example, with the tabs 30 positioned adjacent the long axis. This arrangement would thus define a gap between the edge of the optic portion 28 along its short axis and the inner perimeter surface 20 in the base 16. The gap may enable access for a probe or similar device to pry apart the lens portion 14 from the base portion 12 if separation were needed.

FIG. 4A illustrates a side view of an insertion tool 32 in accordance with exemplary embodiments. The insertion tool 32 may include a housing 33, levers 34, and a nozzle 35. The levers 34 may extend from an interior portion of the housing 33 and may move (e.g., pivot) inward towards a longitudinal axis, L, of the insertion tool 32 (e.g., inward toward a center of the insertion tool 32), as indicated by the arrows 37 The nozzle 35 may be disposed on an end of the insertion tool 32, as shown. The housing 33 may be configured to receive the nozzle 35. In some embodiments, the nozzle 35 may be attachable to the housing 33 so that the nozzle 35 can be coupled and decoupled from the housing 33.

Figure 4B:
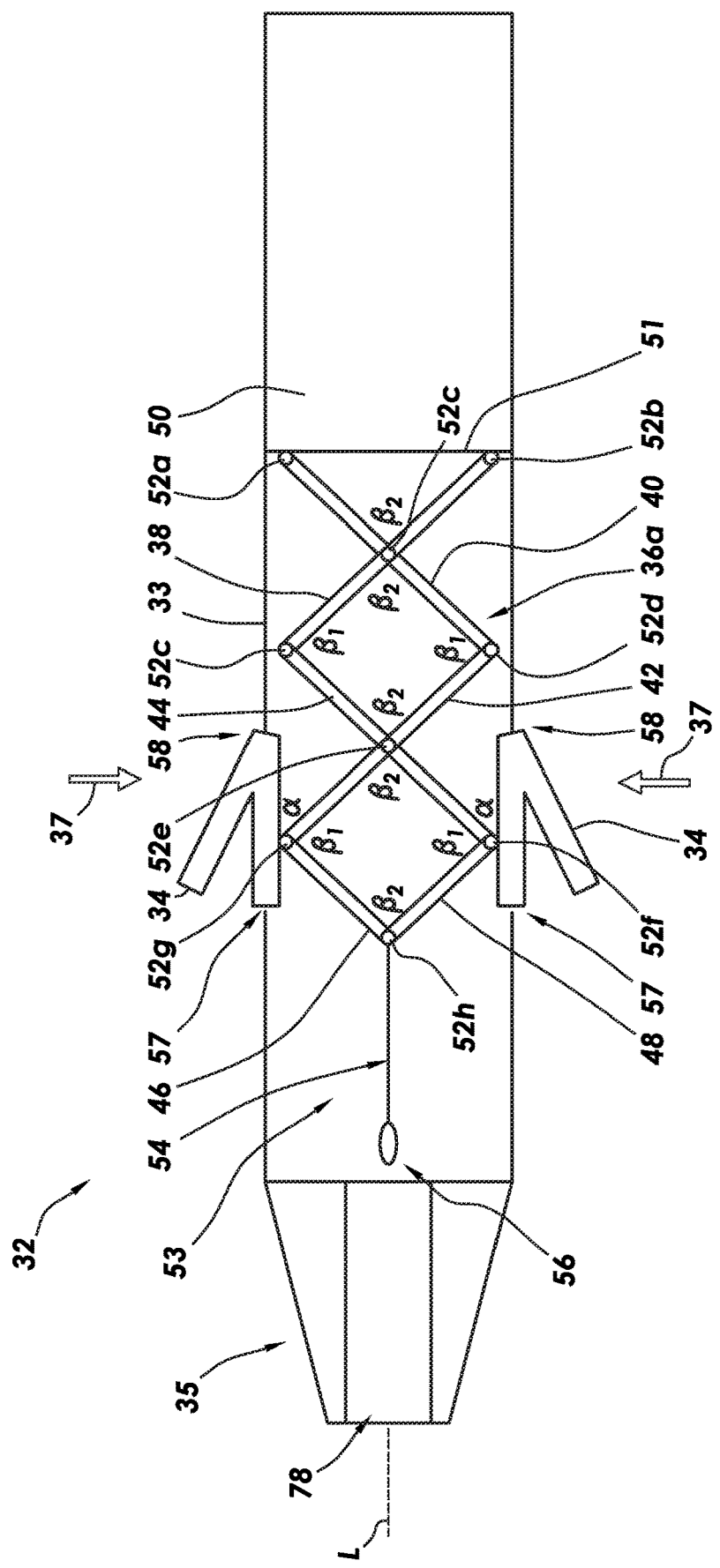
FIGS. 4B and 4C are cross-sections of the insertion tool of FIG. 4A in accordance with embodiments of the present disclosure.
Figure 4C:
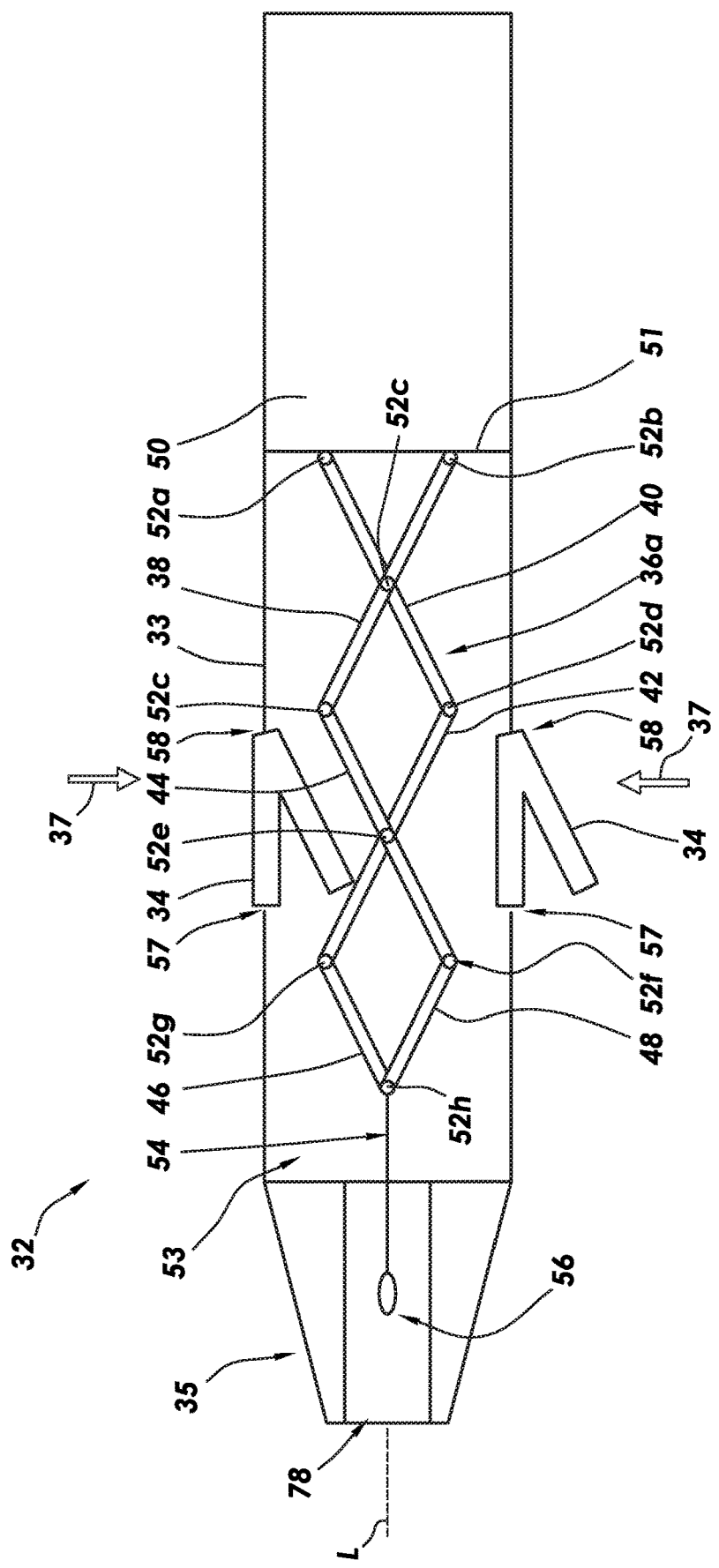

FIGS. 4B and 4C illustrate cross-sections of the side view of the insertion tool 32 of FIG. 4A in accordance with exemplary embodiments. The cross-sections are taken along an entire length (e.g., along L). As shown, the insertion tool 32 further comprises a linkage assembly 36a (e.g., a scissor assembly) positioned within the housing 33. As illustrated, the linkage assembly 36a is in a retracted or initial position. The linkage assembly 36a may be configured to extend along L within the insertion tool 32.

The linkage assembly 36a may include linkages 38, 40, 42, 44, 46, and 48 positioned in a crisscross configuration, as shown, for example. The linkages 38 and 40 may be pivotably coupled to a base 50 that is positioned within and coupled to an interior portion of the housing 33 via joints 52a and 52b. In certain embodiments, the base 50 does not move and is an attachment point for the linkage assembly 36a. The base 50 may include at least one track 51 to allow joints 52a and 52b to move toward or away from L during actuation of the linkage assembly 36a. In certain embodiments, there may be a track 51 for each joint. The track 51 may retain the joints 52a and 52b (e.g., via a lip of the track 51). The joints 52a and 52b may be pivots points and may allow the linkages 38 and 40 to pivot within the joints 52a and 52b as the joints 52a and 52b move within the track 51. The track 51 may extend in a direction perpendicular to L. Joints 52c-52h may pivotably couple the linkages 38, 40, 42, 44, 46, and 48, as shown, and allow axial movement of the linkage assembly 36a similar to the joints 52a and 52b. However, the joints 52c-52h may not be confined by a track, as shown. The joints 52a-52h may be formed by pin and hole connections, for example. That is, pins may extend through holes that are positioned at ends of the linkages, thereby pivotably coupling the linkages to allow axial movement (e.g., axial extension or axial retraction of the linkage assembly 36a) of the linkages 38, 40, 42, 44, 46, and 48 within a bay 53 that is positioned within the housing 33 and in fluid communication with the nozzle 35. The bay 53 may be a compartment that holds a lens component 56.

As shown, the joint 52h (e.g., a leading joint positioned closest to the nozzle 35) may be coupled to a shaft 54 that may be in contact with the lens component 56 at a distal end of the shaft 54, as shown. The shaft 54 may extend longitudinally within the insertion tool 32, as shown. The lens component 56 may include at least one component of the modular IOL 10 shown on FIG. 2, such as the base portion 12 or the lens portion 14.

In certain embodiments, the levers 34 may be rigid members resembling the letter "V" or a triangular shape. The levers 34 may be depressed and pivot or move inward within apertures 57. In certain embodiments, the levers 34 may be attached to a pivot point 58 of the housing 33. The apertures 57 may be fluidly coupled to the bay 53 and may extend from the bay 53 through the housing 33. The joints 52g and 52f (or linkages 42 and 44) may contact levers 34 at an angle α that may be less than 45° (e.g.,)30° when the linkage assembly 36a is configured in the retracted position, as shown. α allows for linkages 42 and 44 to straighten out upon depression of the levers 34. Steeper angles may not allow levers 34 to be depressed with ease, if at all, for example.

FIG. 4C illustrates the linkage assembly 36a in a partially extended position (e.g., see arrow 59 indicating a direction of extension). As the levers 34 are depressed, the levers 34 push against the linkage assembly 36a (e.g., joints 52g and 52f) thereby causing the linkage assembly 36a to straighten and extend toward the nozzle 35. As the linkage assembly 36a straightens, the linkages collapse toward L to axially move the lens component 56 through the nozzle 35 and into a patient's eye, during a procedure. In other words, as the levers 34 are depressed, α decreases causing the shaft 54 to extend axially, as indicated by the arrow 59. Although shown in a partial extension, the linkage assembly 36a may collapse completely to resemble a single member extending from the base 50. When the linkage assembly 36a is in a completely extended position (completely collapsed configuration), the lens component 56 and at least a portion of the shaft 54 extend outside of the nozzle 35. A distance that the shaft 54 moves axially forward may be proportional to a distance the levers move inward (e.g., the distance measured in a direction that is perpendicular to L). In certain embodiments, as the levers 34 are depressed, angles $\beta_1$ formed between the linkages increase, as the angles $\beta_2$ between the linkages decrease.

Figure 5B:
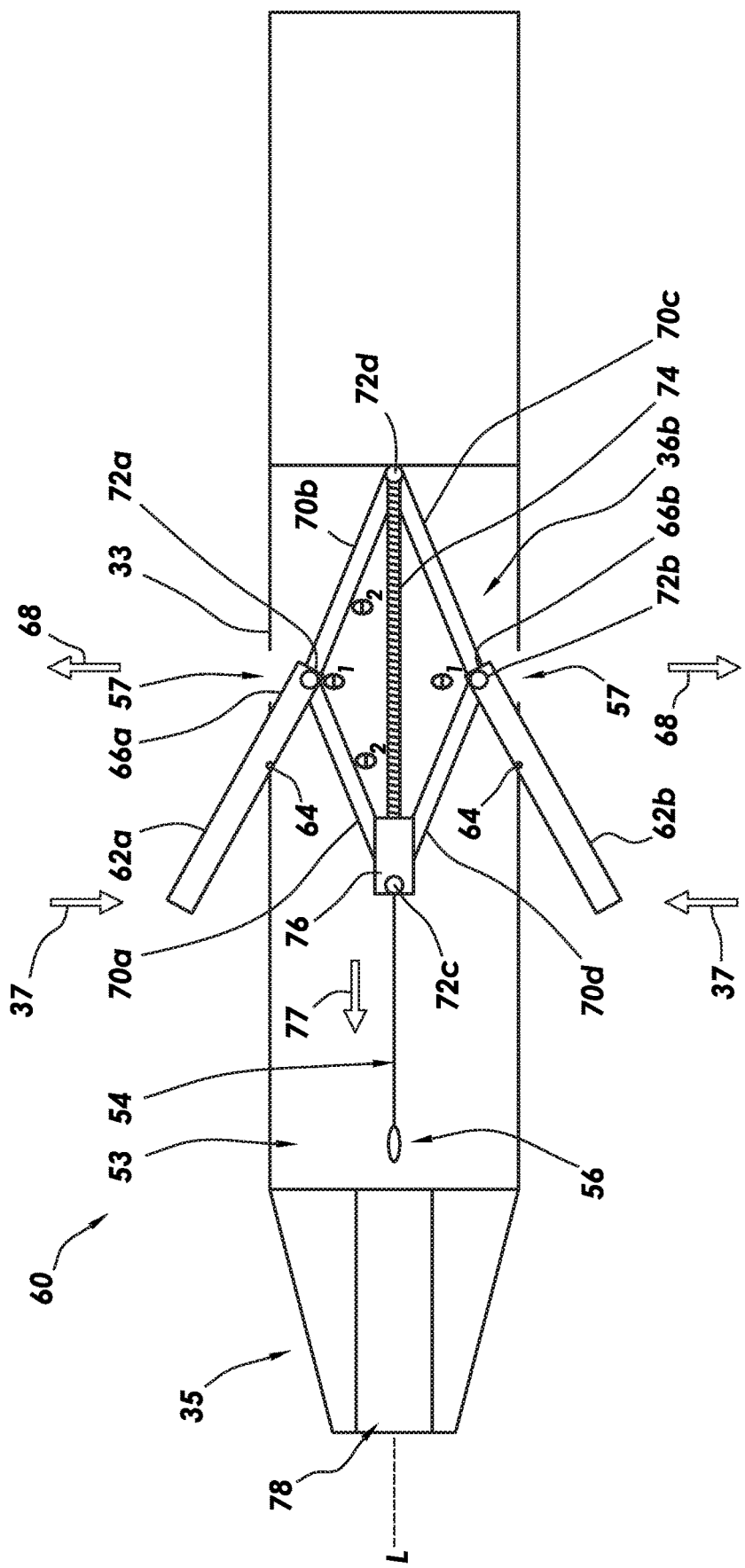
FIGS. 5B and 5C are cross-sections of the insertion tool of FIG. 5A in accordance with embodiments of the present disclosure.
Figure 5C:
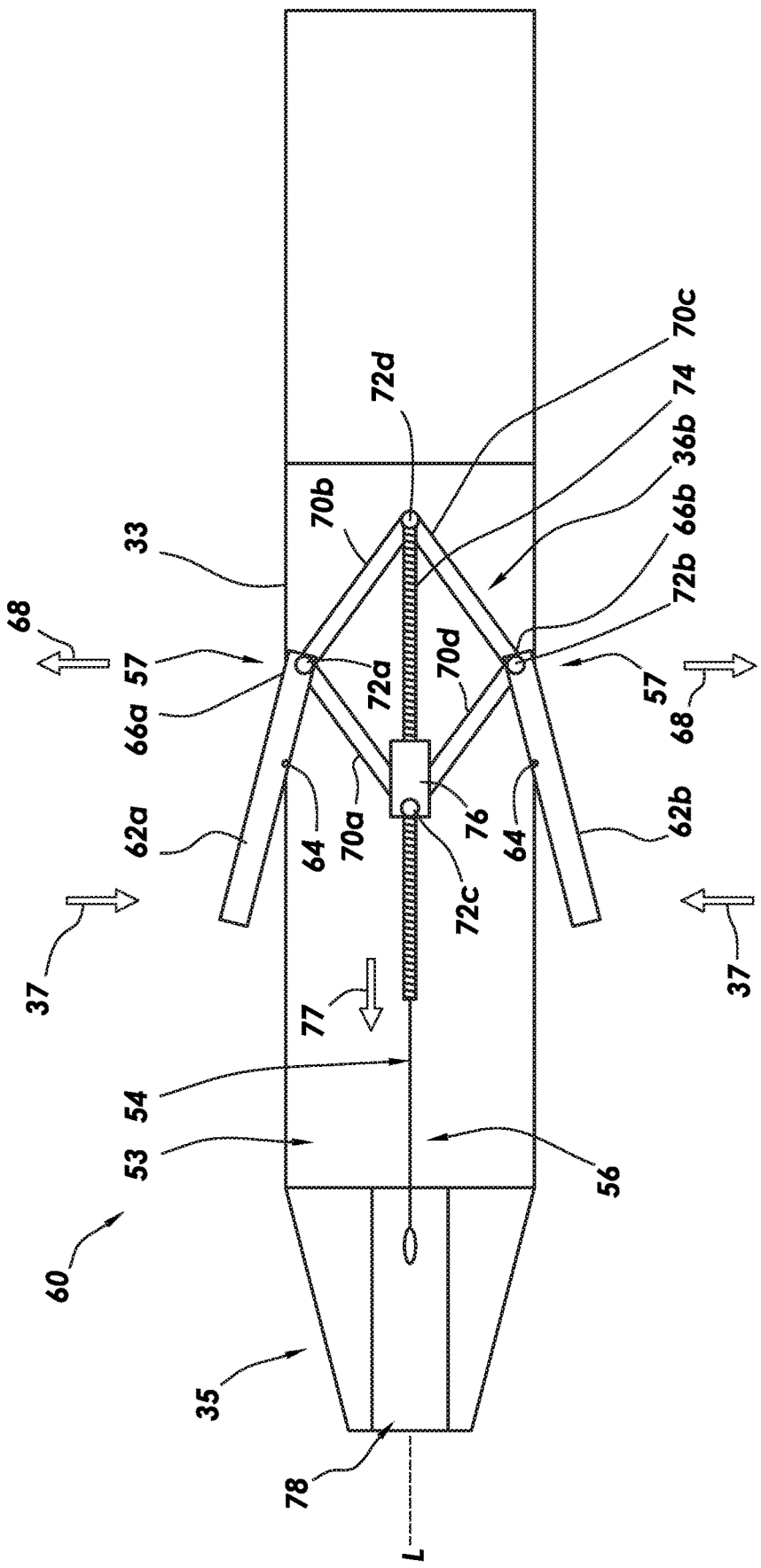

FIGS. 5A-5C illustrate an insertion tool 60. The insertion tool 60 may include levers 62a and 62b that may be positioned at pivot points 64 of the housing 33, as shown on FIG. 5A. The levers 62a and 62b may be elongated members that extend from an exterior of the housing 33 into an interior of the housing 33 (e.g., the bay 53) via apertures 57. As the levers 62a and 62b are depressed (see arrows 37), distal ends 66a and 66b of the levers 62a and 62b, respectively, move away from L (see arrows 68).

The distal end 66a may be pivotably coupled to linkages 70a and 70b via a joint 72a. The joint 72a may also pivotably couple the linkage 70a to the linkage 70b, as shown. The distal end 66b may be pivotably coupled to linkages 70c and 70d via a joint 72b. The joint 72b may also pivotably couple the linkage 70c to the linkage 70d, as shown.

The linkages 70a and 70d (e.g., front linkages positioned closer to the nozzle 35) may be pivotably coupled to each other via a joint 72c. The linkages 70b and 70c (e.g., rear linkages positioned further from the nozzle 35) may be pivotably coupled to each other via a joint 72d. The joints 72a-72d may be similar to the joints as described herein (e.g., joints 52c-52h). The joint 72c may be coupled to the shaft 54, as shown. In particular embodiments, the linkages 70a-70d may be pivotably coupled to each other to form a linkage assembly 36b configured as a parallelogram, as shown, for example.

A rod 74 (e.g., a threaded rod) may extend longitudinally within the bay 53 and may extend through a passage 76. In certain embodiments, the shaft 54 may be axially aligned with and coupled to the rod 74. The passage 76 may be coupled to the joint 72c. In some embodiments, the passage 76 may be coupled to an interior wall of the bay 53 instead of the joint 72c. In particular embodiments, the rod 74 and the passage 76 may form a screw type actuator that converts linear motion to rotational motion, such as a roller screw, for example. Roller screws may also be known as planetary roller screws or satellite roller screws.

As a user depresses the levers 62a and 62b (see arrows 37), the distal ends 66a and 66b move outward (e.g., expand in a direction away from L; see arrows 68, causing the linkages 70a-70d to move (e.g., pivot) and propel the rod 74 axially forward through the passage 76 and toward and through the nozzle 35 (see arrow 77). As the rod 74 moves axially forward, the shaft 54 also moves axially forward along with the lens component 56. In certain embodiments, as the evers 62a and 62b are depressed, angles $\theta_1$ between the linkages decrease as angles $\theta_2$ between the linkages increase, as shown.

In certain embodiments, the insertion tool 32 and the insertion tool 60 may be preloaded. That is, when provided to an end-user, the insertion tools 32 and 60 may have the lens component 56 (e.g., modular IOL 10, base portion 12, and/or lens portion 14) in an unfolded state already present there within and ready to deliver. Having the insertion tools 32 and 60 preloaded with the lens component 56 should reduce the number of steps a user may be required to accomplish before delivering the lens component 56 into a patient's eye. With a reduced number of steps, error and risk associated with delivery of the lens component 56 may be reduced. Further, an amount of time required to deliver the lens component 56 may also be reduced. In some embodiments, the lens component 56 may be pre-loaded into the bay 53.

In an initial position, the lens component 56 may be positioned in the bay 53 prior to the advancement stage. The lens component 56 may be folded (compressed) in the bay 53 as described herein. The lens component 56 may be rolled or folded to reduce a size of the lens component 56. This reduction in size allows delivery of the lens component 56 through a minimally sized incision in the eye.

In the advancement stage, the insertion tools 32 and 60 may advance the lens component 56 from the bay 53 to a dwell position in the deployment channel 78 of the nozzle 35. In some embodiments, the lens component 56 may be folded in the advancement stage. The dwell position may be in the nozzle 35, or may be otherwise situated, for example, in the bay 53.

In the deployment stage, the insertion tools 32 and 60 may advance the lens component 56 from the dwell position and out the nozzle 35 via the deployment channel 78 and into a patient's eye.

An exemplary technique for implantation of the modular IOL 10 into an eye 90 of a patient will now be described with respect to FIGS. 6A-6C.

Figure 6A:
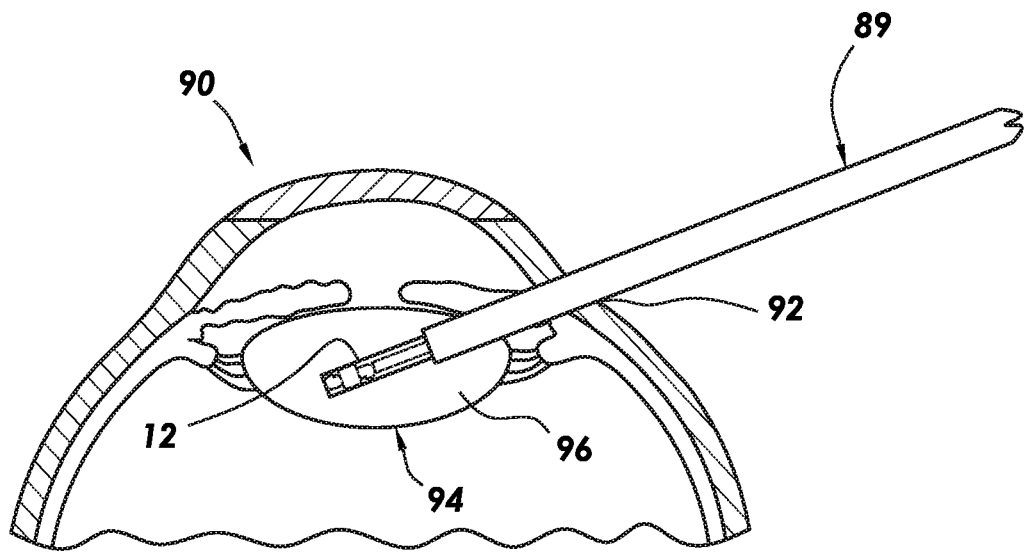
FIGS. 6A-6C illustrate implantation of a modular IOL in accordance with embodiments of the present disclosure.
Figure 6B:
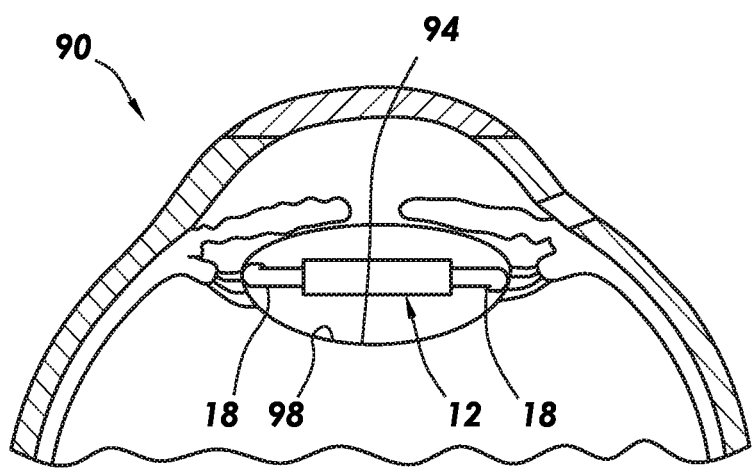

As illustrated on FIG. 6A, an insertion tool 89 (e.g., the insertion tool 32 or the insertion tool 60) may first dispense the base portion 12 into the eye 90 of a patient. In embodiments, an incision 92 may be made in the eye 90 by a surgeon. For example, the incision 92 may be made through the sclera 94 of the eye 90. The incision 92 may be a suitable width or length. Without limitation, the suitable width and/or length may be less than about 4000 microns (4 millimeters). For example, the incision 69 may have a suitable width and/or length of from about 1000 microns to about 400 microns, from about 1000 microns to about 3000 microns, or from about 2000 microns to about 3000 microns. After the incision 92 is made, the nozzle 35 of the insertion tool 89 may be inserted through the incision 92 into an interior portion 96 of the eye 90. The insertion tool 89 may be actuated to dispense the base portion 12 into a capsular bag 98 of the eye 90. This initial movement of the base portion 12 may be performed at any suitable time, for example, before the incision 92 is made. Once the insertion tool 89 is positioned with the nozzle 35 in the eye 90, the insertion tool 89 may then drive the base portion 12 (in a folded or rolled configuration) through the nozzle 35 and into the interior portion 96 of the eye 90. Upon dispensation, the base portion 12 should unfurl and settle within the capsular bag 98 of the eye 90, as shown on FIG. 6B. The haptic extensions 18 may be manipulated, for example, to engage the inside an equator of the capsular bag 98. The haptic extensions 18 may engage the capsular bag 98 to secure the base portion 12 in the capsular bag 98.

Figure 6C:
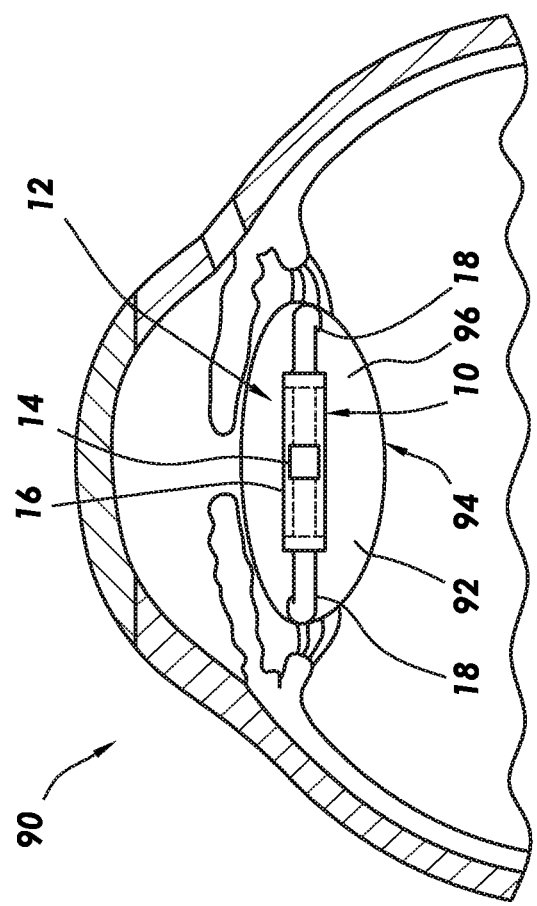

As illustrated on FIG. 6C, the lens portion 14 may be positioned in the interior portion 96 of the eye 90. In the illustrated embodiment, the lens portion 14 is shown positioned in the base 16 of the base portion 12. The lens portion 14 may be delivered in a folded (or rolled configuration) and allowed to unfurl after ejection from the inserter. The lens portion 14 may be positioned in the base 16 of the base portion 12 and secured to the base portion 12, for example, by use of the tabs 30 shown on FIG. 3, to form the modular IOL 10. However, embodiments should not be limited to use of the tabs 30 for interlocking the lens portion 14 and the base portion 12 and other suitable locking mechanisms may be used for securing lens portion 14 to the base portion 12 for forming the modular IOL 10. The base portion 12 may hold the lens portion 14 within the eye 90 so that the lens portion 14 may refract light to be focused on the retina.

Use of the methods and systems described herein may provide numerous benefits and advantages over other IOL delivery systems. For example, the insertion tools including the preloaded IOL, as described herein, improve sterility due to decreased handling by users. Additionally, the insertion tools may allow delivery of the IOL by depressing levers. The levers may provide a mechanical advantage to a user by allowing the user to advance the IOL by applying less force than a direct push mechanism, as well as allowing the user to depress the levers with a single hand. The levers also provide a simple translation of a lever motion to a forward movement of the IOL. Further, the threaded rod allows for a controlled and precise movement of the IOL.

It is believed that the operation and construction of the present disclosure will be apparent from the foregoing description. While the apparatus and methods shown or described above have been characterized as being preferred, various changes and modifications may be made therein without departing from the spirit and scope of the disclosure as defined in the following claims.

What is claimed is:

1. An apparatus for delivery of a lens component into an eye, comprising:
    a nozzle;
    a housing, wherein the nozzle is operatively coupled to the housing;
    a first lever;
    a second lever; and
    a linkage assembly disposed within the housing between and adjacent to the first and second levers, the linkage assembly comprising a plurality of linkages pivotably coupled to each other, wherein the linkage assembly is collapsible through actuation of the first and second levers.

2. The apparatus of claim 1, wherein a first linkage of the plurality of linkages contacts the first lever.

3. The apparatus of claim 2, wherein the first linkage contacts the first lever at an angle that is less than 45°.

4. The apparatus of claim 3, wherein a second linkage of the plurality of linkages contacts the second lever.

5. The apparatus of claim 4, wherein the second linkage contacts the second lever at an angle that is less than 45°.

6. The apparatus of claim 5, wherein the first and second levers are pivotably coupled to the housing.

7. The apparatus of claim 6, further comprising a shaft coupled to the linkage assembly, the shaft positioned to contact the lens component.

8. The apparatus of claim 7, wherein the shaft extends longitudinally within the housing, wherein the nozzle is positioned to receive the shaft.

9. The apparatus of claim 8, wherein a first end of the linkage assembly is coupled to the shaft.

10. The apparatus of claim 9, wherein a second end of the linkage assembly is movably coupled to a base positioned within the housing.

11. The apparatus of claim 10, wherein the first end of the linkage assembly is positioned closer to the nozzle than the second end.

* * * * *